United States Patent [19]

Shoher et al.

[11] Patent Number: 4,940,637
[45] Date of Patent: * Jul. 10, 1990

[54] DENTAL FOIL AND CROWN

[76] Inventors: Itzhak Shoher, 50 Shlomo Hamelech St., Tel Aviv; Aharon Whiteman, 13 J. L. Perez St., Petach-Tikvah, both of Israel

[*] Notice: The portion of the term of this patent subsequent to Jun. 30, 2004 has been disclaimed.

[21] Appl. No.: 948,008

[22] Filed: Dec. 31, 1986

Related U.S. Application Data

[63] Continuation-in-part of Ser. No. 847,228, Apr. 2, 1986, Pat. No. 4,676,751, which is a continuation of Ser. No. 690,650, Jan. 11, 1985, abandoned.

[51] Int. Cl.$^5$ .......................... B32B 15/04; A61C 5/09
[52] U.S. Cl. ..................................... 428/607; 428/669; 428/670; 428/672; 433/218; 433/222.1
[58] Field of Search ............... 428/607, 606, 672, 670, 428/621, 632, 669; 433/207, 208, 218, 222, 223, 227

[56] References Cited

U.S. PATENT DOCUMENTS

| | | | |
|---|---|---|---|
| 145,274 | 12/1873 | Blake | 428/607 |
| 154,446 | 8/1874 | Blake | 428/672 |
| 1,008,845 | 11/1911 | Meier | 428/607 |
| 3,052,983 | 9/1962 | Weinstein et al. | 433/222.1 |
| 4,451,639 | 5/1984 | Prasad | 433/222.1 |
| 4,459,112 | 7/1984 | Shoher et al. | 433/218 |
| 4,492,579 | 1/1985 | Shoher et al. | 433/218 |
| 4,525,433 | 7/1985 | Heywood | 428/672 |
| 4,576,789 | 3/1986 | Prasad | 433/222.1 |
| 4,676,751 | 6/1987 | Shoher et al. | 428/607 |
| 4,698,021 | 10/1987 | Shoher et al. | 428/607 |

*Primary Examiner*—John J. Zimmerman
*Attorney, Agent, or Firm*—E. Liberstein

[57] ABSTRACT

A dental crown restoration which comprises a metal coping and a relatively thick outer coating of a ceramic dental veneer. The metal coping is composed of a lamination of a low fusing temperature precious metal component substantially or entirely of gold and a high-fusing temperature precious metal component. The high fusing component is formed from three layers with one layer composed of from 90 to 100% palladium bounded on both sides by a gold based layer.

4 Claims, 1 Drawing Sheet

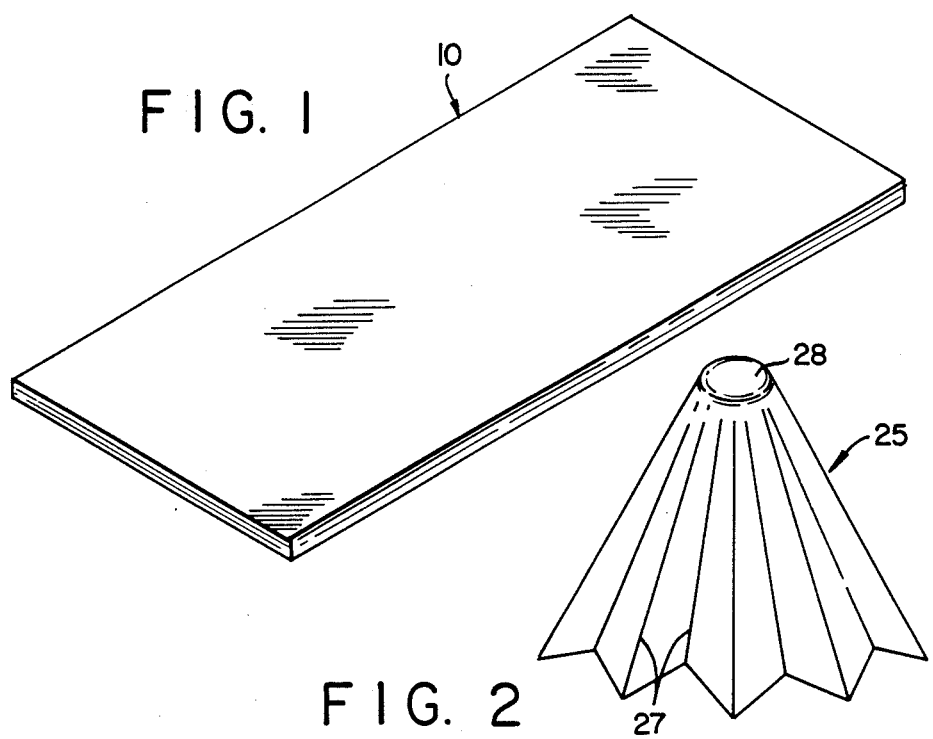
FIG. 1
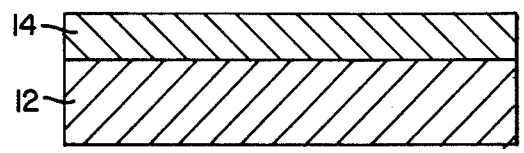
FIG. 2
FIG. 5
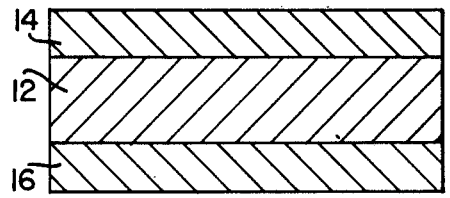
FIG. 3
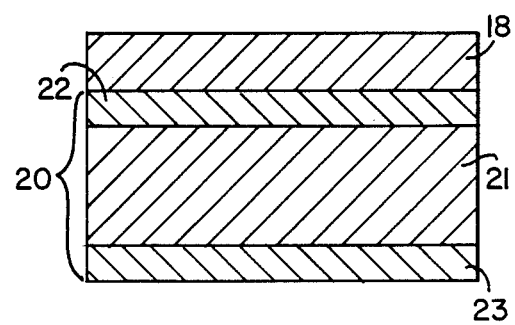
FIG. 4

DENTAL FOIL AND CROWN

This application is a continuation-in-part of U.S. patent application Ser. No. 847,228 filed Apr. 2, 1986, entitled METAL COPING AND CROWN FOR A CERAMOMETAL RESTORATION, now U.S. Pat. 4,676,751, which in turn is a continuation of U.S. patent application Ser. No. 690,650 filed Jan. 11, 1985 and now abandoned.

BACKGROUND OF INVENTION

A new technique for constructing a porcelain to metal crown having a fracture resistance comparable to or greater than the fracture resistance to impact forces of the veneer cast metal crown and which overcomes many of the shortcomings of the conventional porcelain jacket crown is disclosed in U.S. Pat. Nos. 4,273,580 and 4,459,112, respectively. In accordance with U.S. Pat. No. 4,273,580, a precious metal foil, preferably a laminate of several precious metal layers, is swaged about a prepared die of a tooth to form a metal matrix upon which a veneering material such as porcelain is fired. However, unlike the conventional porcelain jacket crown, the metal matrix is not removed or separated from the veneering material but is instead retained as a metal coping for the finished porcelain jacket crown. The metal coping is employed as an understructure in the conventional porcelain to metal cast crown.

The physical strength of the metal coping may be substantially enhanced and the ease of preparing the restoration greatly simplified by converting the metal foil starting material into a preformed coping of predetermined geometry as taught and described in U.S. Pat. No. 4,459,112 referred to above. The metal foil starting material is cut into a circular segment and folded to form multiple folds which are uniformly spaced apart and preferably extend radially from a central unfolded area. This multiple fold geometry makes it easy to adapt the preformed coping to the die without the need for superior skill and craftsmanship and even more importantly increases the strength of the coping. Although the preformed coping as above described has certain advantages, it is not essential to the practice of the present invention. In fact, any preformed shape or method of construction may be used.

A metal coping should function to both protect the tooth abutment and as a structural support for the crown or bridge. In the latter respect, the coping supports the veneer material and provides structural strength and rigidity to the dental restoration. An ideal coping will act as an extension of the vital abutment tooth to protect the tooth against fracture and to resist distortion and displacement from the forces applied when chewing food.

The strength of the metal coping after it is swaged and removed from the die is dependent upon its hardness and rigidity. These characteristics may be satisfied using a precious metal which is known to be hard and relatively rigid such as a composition of platinum. Rigidity is basically controlled by thickness. Conversely, the ability to adapt and swage the preformed coping to the die so as to assure a proper adaptation with accurate marginal fit requires the coping to be highly workable, i.e., it should be soft and flexible. To be flexible the material should be thin. A dental coping should accordingly be of a material composition which is soft and flexible when it is adapted to the die and yet is hard and rigid after adaptation so as to provide the required structural support for the restoration. These apparent contradictory requirements are met by the coping and crown construction of the present invention. The hardness or softness of a metal is determined by measuring its resistance to permanent indentation. A hardness number is assigned to the material using any one of several conventional hardness tests such as the Vickers hardness test, which uses a diamond pyramid indenter.

In the parent application, U.S. Ser. No. 847,228, the metal coping is formed from a metal foil comprising a low fusing temperature component represented by a gold layer superimposed upon a high fusing temperature component represented by a layer substantially of palladium. The palladium layer is preferably disposed between equal layers substantially of gold. It was discovered that this combination of materials will function before sintering as a soft material and after sintering will convert to a harder and more rigid material. It was further discovered that the location of the palladium layer between layers substantially of gold is essential to increase the fracture resistance of the composite and to minimize any distortion from differences in thermal expansion of the metals during heat treatment.

SUMMARY OF THE INVENTION

In accordance with the present invention, the high fusing temperature component can be an alloy composed of a composition of metals which when alloyed will be substantially equivalent in performance to a layer composed substantially of palladium. The thickness of the high fusing temperature component may have to be adjusted based upon the selection of the alloy composition.

As taught in the grandparent application U.S. Ser. No. 690,650, now abandoned, the disclosure of which is herein incorporated by reference, a composite of a soft metal layer and a hard metal layer can upon heat treatment produce a rigid composite structure due to diffusion between the two layers. Thus the invention can be practiced using an alloy of palladium or platinum which is soft and has a relatively low Vickers hardness number for the high fusing temperature component of the metal foil and a gold layer as the low fusing temperature metal component. The high fusing alloy layer may contain one or more high fusing gold alloy layers symmetrically disposed on both sides thereof. Also, the low fusing temperature gold layer may likewise be disposed on both sides of the high fusing temperature component. The low fusing temperature gold layer may also be a gold alloy.

In one embodiment of the present invention, a metal foil is used for forming a dental coping comprising a layer of a high fusing temperature component composed of a precious metal alloy of palladium or platinum and at least one layer of a low fusing temperature precious metal substantially or entirely of gold. In the preferred embodiment, the high fusing temperature metal component is disposed between two gold alloy layers containing up to 100% gold.

In another embodiment of the present invention the metal foil for forming a dental coping comprises a high fusing temperature component including at least three layers in a laminated arrangement.

The dental crown of the present invention comprises a metal coping formed from a metal foil composed of a layer of a high fusing temperature precious metal or alloy of platinum or palladium disposed between two gold alloy layers of up to 100% gold and a ceramic veneer covering all or part of the metal coping.

OBJECTS AND BRIEF DESCRIPTION OF THE DRAWINGS

It is the principal object of the present invention to provide a metal foil for forming a dental coping for a dental crown which is easily adapted to a die yet physically strong after swaging and dimensionally stable in response to heat treatment.

Other objects and advantages of the present invention will become apparent from the following detailed description of the invention when read in conjunction with the accompanying drawings of which:

FIG. 1 is an enlarged perspective of a rectangular segment of a metal foil starting material for forming a cental coping for a dental crown;

FIG. 2 is an end view of one embodiment of the layered construction of FIG. 1 according to the present invention;

FIG. 3 is an end view of an alternate laminated arrangement of the metal foil of FIG. 1 according to the present invention;

FIG. 4 is an end view of yet another alternate laminated arrangement of the metal foil of FIG. 1; and FIG. 5 is a perspective of a preferred dental coping formed from the metal foil of FIG. 1.

DETAILED DESCRIPTION OF THE INVENTION

The metal foil starting material 10 of FIG. 1 is used for forming a dental coping in the preparation of a dental crown. Although it is shown having a rectangular geometry it may likewise have a circular or round geometry. FIGS. 2-4 show alternate layered constructions for the metal foil 10. Each construction includes a high fusing temperature metal layer and at least one low fusing temperature metal layer.

A high fusing temperature for purposes of the present invention means a melting temperature of at least about 1250° to 1300° C. whereas low fusing temperature means a melting temperature substantially equal to the melting temperature of gold. In FIG. 2, a high fusing temperature precious metal layer 12 is shown composed of an alloy of one group of metals including palladium and/or platinum each taken alone, or in combination with each other, and/or in combination with one of the following elements: iridium, rhenium and ruthenium and a second group of metals including gold alone or in combination with one of the following elements: silver and copper. A preferred composition for the high fusing layer 12 should contain up to about 50% of each group of metals with the second group preferably at least about 35% gold with the remainder of the second group divided between copper and silver. The low fusing component 14 is composed substantially or entirely of gold. In FIG. 3 the second low fusing gold layer 16 is shown on the opposite side of the high fusing component 12. A high fusing temperature metal layer of, for example, palladium and gold is relatively soft. Upon heat treatment diffusion of palladium into the low fusing gold layers 14 and 16 occurs to cause an increase in hardness and strength in the composite coping. Heat treatment is recommended before any veneering material is applied to cause some melting of the gold layers 14 and 16 to fill voids and spaces and to form a composite dental coping structure. Heat treatment is also necessary to fire each layer of porcelain or other veneer composition. The location of the high fusing temperature metal layer 12 between two substantially identical gold alloy layers 14 and 16 is preferred in accordance with the teaching of the present invention. This arrangement establishes dimensional stability under heat treatment and reduces the likelihood of distortion from expansion and contraction before and after porcelain baking.

It should be noted that in the embodiment of FIGS. 2 and 3 only a single layer of a palladium and/or platinum gold alloy is required for the high fusing temperature component of the present invention. Moreover, such layer particularly when composed of a palladium alloy and gold may be relatively thick between 25 and 50 microns with 35 microns being preferred. The gold layers may also be somewhat thicker between 8 and 30 microns and preferably about 14 microns in thickness. This increased thickness provides added body which renders the coping less fragile, easier to handle and increases its strength after adaptation.

An alternative multi-layered arrangement is shown in FIG. 4 comprising a low fusing metal layer 18 superimposed over a high fusing ternary lamination 20 including a first layer 21, equivalent in composition to layer 12 of FIG. 2, bounded by gold based layers 22 and 23 respectively. The gold based layers 22 and 23 each contain from 50 to 100% gold and from 0 to 50% of one or more of the following elements in combination: silver, palladium, platinum, iridium, copper and aluminum. The arrangement of FIG. 4 can readily be expanded to include two high fusing temperature metal layers provided each high fusing temperature metal layer is bounded on each side by an equal gold based layer. Also in the embodiment of FIG. 4 gold based layers 22 and 23 need not be single layers but each may instead represent a multiple of gold layers. The use of gold based layers on opposite sides of the palladium and/or platinum alloy layer controls the dimensional stability of the coping under heat treatment and its coefficient of expansion. Regardless of the arrangement, it is preferable for the practice of the present invention to provide symmetrical layers of a gold composition on both sides of the high fusing component as shown in FIGS. 3 and 4. If multiple gold layers are used each side of the palladium or platinum alloy layer should preferably be symmetrical in number of layers, thickness and composition.

A preformed coping 25 as shown in FIG. 5 may be formed using the laminated arrangement of FIGS. 2, 3 or 4 or any other arrangement within the scope of the present invention. The preformed coping 25 may be formed following the procedure taught and described in U.S. Pat. No. 4,459,112. As described in the patent, the metal foil starting material 10 is cut into a blank of circular geometry and folded to form multiple fold lines 27. The fold lines 27 extend from a central unfolded area 28. Other construction techniques may likewise be used to fabricate a preformed coping and of alternate shapes. The preformed coping 25 is then placed over the die (not shown) to adapt the coping to the die using any conventional swaging device. Once the coping is adapted and removed from the die, it is heat treated by placing it over the flame of a Bunsen burner for a short time period based on flame temperature to allow the low fusing temperature gold layer 14 to flow to form a compact metal composite without air pockets. This heat treatment may also be carried out in a furnace at a temperature of about 1020° C. to 1150° C.

After the heating step, porcelain or another veneering material can be directly applied in a conventional manner to form the dental crown of the invention. Acrylic or other polymeric based compositions may be used as the veneering material.

The optimum metal foil is a multi-layer lamination with a high fusing metal layer arrangement of a plurality of platinum and/or palladium layers with high fusing temperature gold alloy layers on opposite sides of each platinum and/or palladium layer and a low fusing temperature gold or gold alloy layer on one or preferably both sides of the high fusing layered arrangement. The platinum and/or palladium layers may each be of an alloy of either palladium alone or in combination with platinum. For example, the high fusing component can be a multi-layer of several layers of palladium with each palladium layer having a high fusing temperature gold layer on opposite sides thereof. A low fusing temperature gold layer is superimposed on one or both sides of the high fusing temperature component.

What we claim is:

1. A metal foil for forming a dental coping in the construction of a dental restoration in which said dental coping has a veneering composition applied thereon following heat treatment of such coping, with said metal foil having one or more layers of a high fusing temperature precious metal consisting essentially of a gold and palladium based composition having a high fusing temperature above the temperature of said heat treatment, and having a low fusing temperature layer of gold or gold alloy on each side of said high fusing temperature layer.

2. A metal foil as defined in claim 1 wherein said high fusing temperature metal further comprises one or more of the following elements: iridium, rhenium, ruthenium, silver copper, platinum and alloys thereof.

3. A metal foil as defined in claim 2 in which said high fusing temperature metal layer has a thickness of between 25 and 50 microns.

4. A dental crown comprising a metal coping formed from a heat treated metal foil composed of one or more high fusing temperature precious metal layer(s) consisting essentially of a palladium and gold based composition and a low fusing temperature layer of gold or gold alloy on each side thereof, with said heat treatment being sufficient to melt said low fusing temperature layer and a dental veneer composed of a ceramic or polymeric based composition covering part or all of the coping.

* * * * *